United States Patent [19]

Gresham

[11] Patent Number: 4,604,283

[45] Date of Patent: Aug. 5, 1986

[54] HOOF CONDITIONER AND DRESSING AND METHODS OF USE

[76] Inventor: Anne L. Gresham, 5809 Warren Farm Rd., Rte. 2, Hiram, Ga. 30141

[21] Appl. No.: 756,923

[22] Filed: Jul. 17, 1985

Related U.S. Application Data

[63] Continuation of Ser. No. 603,785, Apr. 24, 1984, abandoned.

[51] Int. Cl.⁴ .................. A61K 31/79; A61K 33/18
[52] U.S. Cl. .................................. 424/80; 424/150
[58] Field of Search ............................ 424/80, 150

[56] References Cited

U.S. PATENT DOCUMENTS

| | | | |
|---|---|---|---|
| 934,515 | 9/1909 | Fulton et al. | 424/150 |
| 1,596,651 | 8/1926 | Bryant | 424/150 |
| 2,550,622 | 4/1951 | Taub | 424/150 |
| 2,776,924 | 1/1957 | Martin | 424/80 |
| 3,152,951 | 10/1964 | Perlman | 424/150 |
| 3,210,248 | 10/1965 | Feldmann et al. | 424/239 |
| 3,441,645 | 4/1969 | McKissick et al. | 424/61 |
| 3,489,690 | 1/1970 | Lachampt | 252/308 |
| 3,671,545 | 6/1972 | Halpern | 424/80 |
| 3,887,702 | 6/1975 | Baldwin | 424/61 |
| 3,928,561 | 12/1975 | Baldwin | 424/61 |
| 3,989,817 | 11/1976 | Mayer | 424/61 |
| 4,017,407 | 4/1977 | Cantor et al. | 424/150 |
| 4,070,451 | 1/1978 | Price | 424/61 |
| 4,226,858 | 10/1980 | Pfirrmann et al. | 424/195 |
| 4,288,428 | 9/1981 | Föll et al. | 424/80 |
| 4,401,651 | 8/1983 | Knutson | 424/80 |

OTHER PUBLICATIONS

*Merck*, 9th ed., Abst. 2429, 9525, 9705 (1976).

*Primary Examiner*—Jerome D. Goldberg
*Assistant Examiner*—F. Abramson
*Attorney, Agent, or Firm*—Kilpatrick & Cody

[57] ABSTRACT

A hoof conditioner and dressing and methods of use. The conditioner and dressing is an oil in water emulsion that contains petrolatum, anhydrous lanolin, cod liver oil fortified with vitamins A and D, wheat germ oil fortified with vitamins A and D and containing vitamin E, urea and Povidone-Iodine solution. It not only acts to retain moisture already in the hoof, but the anhydrous lanolin and urea also hydrate the hoof. The Povidone-Iodine solution provides free iodine to the hoof over a prolonged period of time to promote growth, to act as a counter-irritant, and to kill the bacteria, fungi, and viruses that are often present in the hoof. The conditioner and dressing is semi-solid at room temperature and is easily applied to the hoof and pastern area, but melts when subjected to the body temperature of the animal and is thereby readily absorbed.

1 Claim, No Drawings

HOOF CONDITIONER AND DRESSING AND METHODS OF USE

This is a continuation of my copending application Ser. No. 603,785 filed Apr. 24, 1984, now abandoned.

BACKGROUND OF THE INVENTION

This invention pertains to compositions for treating animal, and particularly horses', hooves. Proper care of a horse's hooves, especially those of a performance horse or a work horse, is essential, because dry, cracked or otherwise damaged hooves are uncomfortable to a horse and can render him lame and unable to hold shoes, run, hunt, or perform his tasks. The keratinous tissue of a hoof is constantly subjected to an environment which promotes deterioration, including dirt, dust, bacteria, gravel and the like. The horse's great weight placed on his hooves promotes dryness, cracking and chipping, especially when combined with this environmentally caused deterioration. Because a horse must be on his feet during every phase of his life, including while sleeping, healthy hooves will allow him to perform more effectively and will ensure that he and his owner lead more comfortable lives.

Previous compositions have been made and used for the purpose of improving the condition of horses' hooves. U.S. Pat. No. 4,070,451 issued Jan. 24, 1978 to Price ("Price"), for instance, discloses an emulsion including glycerol stearate, petrolatum, lanolin wax, lanolin alcohols, stearic acid, mineral oil and paraffin to prevent or counteract drying, cracking or chipping of the horses. Hydrolized animal protein and imidazolinidyl urea are added as nutritional agents. Surfactants may also be added to the Price composition, and vitamin E may be added as an antioxidant and to fortify the hoof tissues. U.S. Pat. No. 3,989,817 issued Nov. 2, 1976 to Mayer ("Mayer") discloses treatment of animal finger and toenails with walnut oil. The walnut oil is said to increase the hardness of the nails, and is suspended in a neutral base carrier such as a water-in-oil emulsion. A water soluble iodide salt such as potassium iodide may be added as a promoter or catalyst.

Other preparations have utilized various oils and emulsions primarily aimed at retaining moisture already in the hoof.

SUMMARY OF THE INVENTION

The present invention comprises a water-in-oil emulsion of petrolatum, anhydrous lanolin, cod liver oil fortified with vitamins A and D, wheat germ oil fortified with vitamins A and D and including vitamin E, urea and Povidone-Iodine solution. Compositions of the invention not only retain moisture already present in an animal's hooves, but their hydrating agents anhydrous lanolin and urea also add to that moisture. Vitamins A and D in the cod liver oil and wheat germ oil nourish the keratinous tissue and promote healing. The Povidone-Iodine solution acts as a counter-irritant, and slowly releases iodine over a period of time. The Iodine continuously acts as an antibacterial, a virucide, and a fungicide. Thus, hydrating materials, nourishing agents, and Iodine are applied in one application of compositions of this invention. Because these compositions are semi-solid at room temperature but melt when subjected to the animal's body temperature, these ingredients are easily applied to the hoof in a single application, but are absorbed readily and effectively.

Because of these ingredients, compositions of this invention promote immediate and consistent improvement and growth when absorbed by the hoof. They are typically applied daily to the complete hoof, including deeply into the heel and at least one inch above the coronary band. These compositions assist in healing extremely dry hooves and hooves with failures such as quarter cracks, especially when applied to the sole and frog of the hoof and massaged into the pastern area up to the fetlock.

It is therefore an object of the present invention to provide a hoof conditioner and dressing which not only acts to retain the moisture present in the hoof, but also acts to hydrate the hoof.

It is a further object of the present invention to provide a hoof conditioner and dressing which nourishes and lubricates the hoof, promotes growth and healing, and kills certain bacteria, fungi and viruses.

It is further object of the present invention to provide a hoof conditioner and dressing which is an oil-in-water emulsion semi-solid at room temperature and easily applied to the hoof, but is melted by the animal's body temperatures and is readily absorbed.

It is a further object of the present invention to provide a hoof conditioner and dressing that provides free iodine to the hoof over a period of time to act as a continuous counter-irritant, bacteriacide, fungicide, and virucide.

It is another object of the present invention to provide methods of treating animal, and particularly horse, hooves using the hoof conditioner and dressing of the present invention in order to promote healing, flexibility, growth, suppleness and healthiness of the hooves, and to make racing, hunting, walking, working, standing and life in general more comfortable for the horse or other animal.

Other objects, features and advantages of the present invention will become apparent with reference to the balance of the specification and claims herein.

DETAILED DESCRIPTION

The above-mentioned ingredients of the compositions of this invention are present as follows, by volume:

| | |
|---|---|
| Petrolatum | 25–50% |
| Anhydrous Lanolin U.S.P. | 10–40% |
| Cod Liver Oil, fortified with vitamins A & D | 5–30% |
| Wheat Germ Oil fortified with vitamins A & D and containing vitamin E | 5–30% |
| Urea U.S.P. in 20% aqueous solution | 2–15% |
| Povidone-Iodine solution (10%) | 2–15% |

Petrolatum is employed as a protective and as a base or carrier for stabilizing consistency of compositions of the present invention [E. Martin, Remington's Pharmaceutical Sciences 1421 (1980); G. Wilson and Duerge, Textbook of Organic Medicinal and Pharmaceutical Chemistry 119 (1966)] Petrolatum NF or White Petrolatum U.S.P. may be utilized.

Anhydrous Lanolin, an animal fat, is employed for, among other things, its water absorption properties, its emulsifying and emollient properties and its contribution to the ability of compositions of the present invention to be absorbed readily upon topical application. It absorbs a large amount of water, and thus promotes hydration when the compositions of the present invention are applied to the hoof. [E. Martin, supra, at 1423]

Cod liver oil fortified with vitamins A and D is employed as a natural source of vitamins A and D, and because it is rich in iodine. [E. Martin, supra.] Vitamin A has been termed the "anti-infective" vitamin, and is employed because it tends to increase the power of the epithelial surfaces to resist local infection, in organisms suffering from a vitamin A deficiency. [Id. at 1079] Vitamin D is an antirachitic vitamin, and useful in these compositions for promoting calcification of the bony structures. [Id.] Veterinary grade cod liver oil is preferably used in the present invention, and is preferably fortified with 2750 U.S.P. units of vitamin A per ounce and 750 U.S.P. units of vitamin D per ounce.

Wheat germ oil is included as an excellent source of glycerides of fatty acids. It is a natural source of vitamin E, a vitamin that is useful when topically applied because of its anti-oxidant properties. Vitamin E also speeds healing of wounds and helps prevent build-up of scar tissue. Wheat germ oil is an excellent moisturizer and helps increase the hoof's absorption of vitamins A and D. Preferably, veterinary grade wheat germ oil is used, and is fortified with vitamin A acetate and D activated animal sterol to supply essential fatty acids. In the preferred embodiment, veterinary grade wheat germ oil is fortified with 30,000 U.S.P. units per ounce of vitamin A and 5,000 U.S.P. units per ounce of vitamin D, and contains not less than 100 U.S.P. units per ounce of vitamin E.

Urea U.S.P., preferably in a 20% aqueous solution is included to assist in hydration of and removal of excess keratin from the hoof. [E. Kastrup, Facts and Comparisons Drug Information, 608 (1982)]

Povidone-Iodine (Polyvinylpyrrolidone-iodine complex) is a topical anti-infective which is available commercially as BETADINE ® solution. It is included because it assists in growth of new horn, [O. Siegmund, The Merck Veterinary Manual 557 (1979)], acts as a counter-irritant, and also as a bacteriacide, fungicide and virucide. Povidone-Iodine is preferred in the present invention because it gives off free iodine over a period of time. Iodine has been described as the best all around antiseptic, in appropriate dilutions. [E. Martin, supra, at 1235] The timed release of iodine results in longer and greater protection against bacterial and fungal infections so prevalent in horse hooves. A ten percent solution of Povidone-Iodine is preferred, such as BETADINE ® solution (10% Povidone-Iodine). A typical formulation for Povidone-Iodine product (1000 liters) is:

| Povidone-Iodine Solution | |
| --- | --- |
| (a) Povidone-Iodine Powder | 125 kg |
| (b) Sodium Phosphate (tribasic) | 7.5 kg |
| (c) Triton X-114 | 4.0 kg |
| (d) Water (q.s.) | 1000 liters |
| Analysis | |
| (a) pH | Less than 6.0 |
| (b) Density | 1.03 to 1.04 |
| (c) Viscosity | 15 to 25 cp |
| (d) Superficial Tension | 31 to 33 dynes/cm |
| (e) Available Iodine | 1.15-1.20% |

(Triton X is polyethylene glycol p-isooctylphenyl ether)

In the preferred embodiment of the present invention, the ingredients are present by volume as follows:

| | |
| --- | --- |
| White Petrolatum U.S.P. | 40% |
| Anhydrous Lanolin U.S.P. | 25% |
| Cod Liver Oil (Veterinary Grade) fortified with 2750μ vitamin A per ounce and 750μ vitamin D per ounce | 12.5% |
| Wheat Germ Oil (Veterinary Grade) fortified with 30,000μ vitamin A per ounce and 5,000μ vitamin D per ounce and containing 100μ vitamin E per ounce | 12.5% |
| Urea U.S.P. in a 20% aqueous solution | 5% |
| Povidone-Iodine solution (10%) | 5% |

Example I shows the method in which this preferred embodiment of the present invention is prepared:

EXAMPLE I

The composition of the preferred embodiment of the present invention is prepared in a double-wall calibrated tank which is heated by circulating hot water through the space between the two walls. The water temperature is thermostatically controlled to obtain proper temperature to melt and combine the ingredients.

The petrolatum is measured into the tank. Its melting point is between 38 and 60 C. When melted, the temperature is brought to 50 C.

The anhydrous lanolin, whose melting point is between 36 and 42 C., is then added to the petrolatum. When the anhydrous lanolin is melted, the mixture is blended thoroughly with a high speed mixer, and its temperature is brought once again to 50 C.

When 50 C. is reached, the cod liver oil and wheat germ oil are added, the blending is continued, and the temperature is once again brought to 50 C.

The Povidone-Iodine solution is added and blended well, and the temperature is again brought to 50 C.

Finally, the urea is added and blended well. The temperature of the mixture is gradually reduced to 38 C. while high-speed blending continues to obtain proper emulsification of the oil phase with the aqueous phase. As the mixture gradually cools, the petrolatum and the anhydrous lanolin hold the aqueous solution and the oils to form a water-in-oil emulsion in semi-solid form. The emulsion is packaged in proper containers and allowed to cool to room temperature. This semi-solid form has proved to be easily applied to the hoof, yet melts at the horse's body temperature. It exhibits an extremely high absorption rate and allows prolonged action of the active ingredients on the hoof and skin.

This preferred embodiment of the present invention is readily absorbed upon application to the hoof, promotes immediate and consistent improvement in the existing hoof, and promotes growth of new healthy horn. This composition is preferably applied and massaged daily into the complete hoof, deeply into the heel, and at least one inch above the coronary band. For extremely dry hooves or problems such as sand cracks, toe cracks or quarter cracks, it is preferably applied and massaged into the sole and frog of the hoof and massaged into the pastern area up to the fetlock.

Examples IV through VII are descriptions of previous use of the composition of the preferred embodiment of the present invention.

EXAMPLE II

The following ingredients are mixed and applied according to the steps recited in Example I, in the following proportions by volume:

| | |
|---|---|
| White Petrolatum U.S.P. | 50% |
| Anhydrous Lanolin U.S.P. | 10% |
| Cod Liver Oil (Veterinary Grade) fortified with 2750μ vitamin A per ounce and 750μ vitamin D per ounce | 5% |
| Wheat Germ Oil (Veterinary Grade) fortified with 30,000μ vitamin A per ounce and 5,000μ vitamin D per ounce and containing 100μ vitamin E per ounce | 5% |
| Urea U.S.P. in a 20% aqueous solution | 15% |
| Povidone-Iodine solution (10%) | 15% |

This formula provides a conditioner having a fairly thin consistency resulting from the relatively great proportion of aqueous phase.

EXAMPLE III

The following ingredients are mixed and applied in the following proportions by volume according to the steps recited in Example I, with the exception that the temperature of the petrolatum is brought to 70 C. and the temperature of the mixture is returned to 70 C. following the addition of each ingredient:

| | |
|---|---|
| White Petrolatum U.S.P. | 25% |
| Anhydrous Lanolin U.S.P. | 40% |
| Cod Liver Oil (Veterinary Grade) fortified with 2750μ vitamin A per ounce and 750μ vitamin D per ounce | 5% |
| Wheat Germ Oil (Veterinary Grade) fortified with 30,000μ vitamin A per ounce and 5,000μ vitamin D per ounce and containing 100μ vitamin E per ounce | 25% |
| Urea U.S.P. in a 20% aqueous solution | 3% |
| Povidone-Iodine solution (10%) | 2% |

This formula provides a conditioner that is not as readily absorbed into the hoof as the conditioner of Example I, but one which includes relatively great amounts of vitamin E and is effective in achieving the objects of the present invention.

EXAMPLE IV

A horse who had been a World's Champion 5-gaited saddlebred, but who had been plagued with bad hooves almost all of his life, was treated with the composition. He had had a painful quarter crack on his front right hoof for approximately five months before application. Many hoof products had been used, but the crack would not grow out. With the use of the present composition, applied daily to the hoof and pastern area, the quarter crack grew out at a measured rate of ¼ inch per week. In eight weeks the horse was able to have shoes replaced and to begin training again.

EXAMPLE V

The composition was applied to the hooves of a 27 year old gelding who had foundered, causing the sole and frog of the hooves to drop, putting pressure on the frog and thereby causing him to be in severe pain, even while only walking. At his age, hoof growth was less than the normal rate of growth of a younger, healthy horse. The composition was applied daily for 10 weeks. His hooves grew approximately ¼ inch per week, giving him relief from the painful founder damage. He was able to grow good new hooves which were pliable and flexible. Continued daily application of the composition allowed the horse to maintain healthy, strong, and flexible hooves with improved rate of growth.

EXAMPLE VI

The composition was applied to the hooves of a 5 year old quarter horse mare with severely dry, cracked hooves. The hooves were so dry that they were almost chalky, and would not hold shoes. Immediately improvement was seen from the moisturizing effects of the composition. In 12 weeks the old hoof was grown out, and the new hooves were very moist, healthy, and able to hold shoes. There was no loss of hoof later from breaking when the shoes were removed to re-set. These healthy hooves are maintained with daily use of the composition.

EXAMPLE VII

The composition was used on a champion paint horse who had injured a hoof in an accident, and who suffered a horizontal crack in the coronary band of the hoof. The horse had been given up for the show season because of the pain in that hoof preventing his training and performance. With daily application of the composition he was able to return to training in 6 weeks, and was shown in 8 weeks. The crack had grown out 2 inches in 8 weeks and was no longer painful to the horse.

It should be noted that the normal rate of hoof growth of horses is approximately ⅓ inch per month for healthy horses. With daily application of compositions of this invention, the hoof is stimulated to grow approximately ¼ inch per week, or 1 inch per month. This is approximately three times the normal rate of growth.

Although the specific compositions set forth above are preferred, it will be apparent to those skilled in the art that other compositions falling within the above-indicated ranges also provide the features and advantages of the present invention.

I claim:

1. A composition for treatment of horse hooves consisting of the following ingredients in percentages by volume:

| | |
|---|---|
| Petrolatum | 40% |
| Anhydrous Lanolin, U.S.P. | 25% |
| Veterinary grade cod liver oil, fortified with 275μ vitamin A per ounce and 750μ vitamin D per ounce | 12.5% |
| Veterinary grade wheat germ oil, fortified with 30,000μ vitamin A per ounce, 5000μ vitamin D per ounce and containing 100μ vitamin E per ounce | 12.5% |
| Urea in a 20% by volume aqueous solution | 5% |
| [Betadine ® 10% Povidone-Iodine solution] 10% Povidone-Iodine solution | 5% |

* * * * *